(12) United States Patent
O'Brien et al.

(10) Patent No.: US 8,447,630 B2
(45) Date of Patent: May 21, 2013

(54) SYSTEMS AND METHODS FOR MANAGING PERMISSIONS FOR INFORMATION OWNERSHIP IN THE CLOUD

(75) Inventors: Richard J. O'Brien, Lisle, IL (US); Andrew M. Gallant, Rockville, MD (US)

(73) Assignee: Payment Pathways, Inc., Lisle, IL (US)

( * ) Notice: Subject to any disclaimer, the term of this patent is extended or adjusted under 35 U.S.C. 154(b) by 239 days.

(21) Appl. No.: 12/892,187

(22) Filed: Sep. 28, 2010

(65) Prior Publication Data

US 2011/0016536 A1 Jan. 20, 2011

Related U.S. Application Data

(63) Continuation-in-part of application No. 11/592,510, filed on Nov. 3, 2006, now Pat. No. 7,945,511, which is a continuation-in-part of application No. 10/786,023, filed on Feb. 26, 2004, now Pat. No. 7,831,490.

(60) Provisional application No. 60/450,754, filed on Feb. 28, 2003.

(51) Int. Cl.
*G06F 19/00* (2011.01)

(52) U.S. Cl.
USPC .............................................................. 705/3

(58) Field of Classification Search
USPC .............................................. 705/3, 9, 14, 21
See application file for complete search history.

(56) References Cited

U.S. PATENT DOCUMENTS

| | | | |
|---|---|---|---|
| 5,031,098 A * | 7/1991 | Miller et al. ..................... | 705/21 |
| 5,677,955 A | 10/1997 | Doggett | |
| 6,173,272 B1 | 1/2001 | Thomas | |
| 6,317,745 B1 | 11/2001 | Thomas | |
| 6,609,113 B1 | 8/2003 | O'Leary | |
| 6,671,696 B1 | 12/2003 | Holcombe | |
| 6,856,975 B1 | 2/2005 | Inglis | |
| 6,947,897 B2 * | 9/2005 | Lortscher et al. .......... | 705/14.36 |
| 7,136,869 B2 | 11/2006 | Holcombe | |
| 7,158,955 B2 | 1/2007 | Diveley | |
| 7,165,052 B2 | 1/2007 | Diveley | |
| 7,213,748 B2 | 5/2007 | Tsuei | |
| 7,225,156 B2 | 5/2007 | Fisher | |
| 7,349,843 B1 | 3/2008 | Beck | |
| 7,742,884 B2 | 6/2010 | Oda | |
| 2002/0062281 A1 | 5/2002 | Singhal | |
| 2002/0077978 A1 | 6/2002 | O'Leary | |
| 2002/0111886 A1 | 8/2002 | Chenevich | |
| 2002/0147625 A1 * | 10/2002 | Kolke, Jr. ......................... | 705/9 |
| 2003/0046112 A1 * | 3/2003 | Dutta et al. ..................... | 705/3 |
| 2003/0089768 A1 | 5/2003 | Page | |
| 2003/0126075 A1 | 7/2003 | Mascavage | |
| 2004/0030645 A1 | 2/2004 | Monaghan | |
| 2004/0059672 A1 | 3/2004 | Baig | |
| 2004/0088219 A1 | 5/2004 | Sanders et al. | |
| 2004/0143552 A1 | 7/2004 | Weichert | |

(Continued)

OTHER PUBLICATIONS

Monaghan's, U.S. Appl. No. 61/366,029, filed Jul. 23, 2010.

(Continued)

*Primary Examiner* — John A. Pauls
(74) *Attorney, Agent, or Firm* — Troutman Sanders LLP

(57) ABSTRACT

The present invention relates to a central (root) directory and the synchronization of unique identifiers associated with a payment addresses and permission preferences at different institutions. In a preferred embodiment, each unique identifier associates an account owner's permissions preference for the release of personal identifying information without the need for transaction-by-transaction explicit permissions or blanket implicit permissions. An asset transfer deposit account (for information and/or monetary assets) may be set up as a deposit only account. In this way, the present invention can be effective in eliminating many privacy concerns of account owners and security requirements of an information asset repository.

43 Claims, 6 Drawing Sheets

U.S. PATENT DOCUMENTS

| | | | |
|---|---|---|---|
| 2004/0148252 | A1 | 7/2004 | Fleishmah |
| 2004/0181450 | A1 | 9/2004 | Yamada et al. |
| 2004/0236681 | A1 | 11/2004 | Modigliani et al. |
| 2005/0131757 | A1 | 6/2005 | Chan et al. |
| 2005/0149439 | A1 | 7/2005 | Suisa |
| 2005/0259658 | A1 | 11/2005 | Logan et al. |
| 2007/0106612 | A1 | 5/2007 | O'Brien |
| 2009/0006124 | A1 | 1/2009 | Sinclair et al. |
| 2009/0013375 | A1 | 1/2009 | MacIntosh et al. |
| 2009/0125523 | A1 | 5/2009 | Fitzpatrick et al. |
| 2010/0124322 | A1 | 5/2010 | Bill |
| 2010/0138902 | A1 | 6/2010 | Shelton |
| 2010/0153407 | A1 | 6/2010 | Krislov |

OTHER PUBLICATIONS

Monaghan's, U.S. Appl. No. 61/377,362, filed Aug. 26, 2010.

No Author, Directory Management Leader NetVision, Inc., Introduces Affordable Software-Leasing Program (PR Newswire, Nov. 22, 1999).

"Technoglogy Journal-Check It Out—The Web is suddenly crowded with online-payment services; Here's how they compare", Will Morton, Asian Wall Street Journal, New York, NY; Dec. 10, 2001, p. T.8.

"Pay it on the Net", Brice Scheschuk, CMA Management, Hamilton, Jun. 2001, vol. 75, Issue. 4; p. 30-34.

"Credit-Card Firms Get Into Web Game—Online Payment Initiatives Are a Must", Sapsford et al., Asian Wall Street Journal, New York, NY, Apr. 3, 2001, p. N.1.

"Still Waiting for the E-mail and Faxes to Start Coming in?", Brooks, Andree, New York Times, (Late Edition, East Coast), New York, NY, Dec. 19, 1996, p. C.7.

International Search Report, PCT Appin. No. PCT/US06/43173, Jul. 21, 2008.

International Search Report dated Dec. 28, 2011.

\* cited by examiner

SYSTEMS AND METHODS FOR MANAGING PERMISSIONS FOR INFORMATION OWNERSHIP IN THE CLOUD

CROSS REFERENCE TO RELATED APPLICATIONS

This application is a continuation-in-part of U.S. patent application Ser. No. 11/592,510, filed Nov. 3, 2006, now U.S. Pat. No. 7,945,511, which is a continuation-in-part of U.S. patent application Ser. No. 10/786,023, filed Feb. 26, 2004, now U.S. Pat. No. 7,831,490, which claims priority to U.S. Provisional App. No. 60/450,754, filed Feb. 28, 2003. The entire contents of those applications are incorporated herein by reference.

FIELD OF INVENTION

The present invention relates generally to information transfer, storage and retrieval, and more specifically, to a networked based computer system and method for establishing explicit permissions and/or privacy preferences and for implementing the transfer, storage and retrieval of select information based on these permissions and preferences.

BACKGROUND

Few bankers working today remember depositors abandoning banks in favor of money market funds when those instruments first arrived in the seventies. With tidal force, bank liquidity eroded and the profits of non-bank financial institutions swelled. Unstoppable wave upon wave of cash withdrawals stressed the balance sheets of banks for more than a decade.

During this time, Non-Interest Income (e.g. transaction fees) from the credit card industry became the most important new source of revenue for banks. It was inflation-proof, popular with customers and wildly profitable. The card business evolved, adding the Debit Card product and its (popular with bankers) Insufficient Funds Penalty fee.

Now, for various reasons, the fees associated with credit & debit cards (hereinafter referred to as bankcards) are under pressure from merchants and regulators. New economic models alleviate this pressure by the organization and selling of information derived from transaction events instead of assessing fees as a percentage of the transaction value. Ownership rights of this information need to be asserted, assigned and tracked.

For generations, long strings of numbers have been used as account identifiers. Unfortunately, long numeric strings of numbers were hard to remember, so it became a common practice to use magnetic stripes and embossed numbers on plastic cards to supply the important account information to the merchant. The merchant submits the number to a payment processing network, which routes it to the consumer's financial service provider for the automatic debiting of his credit account or his demand deposit account (a.k.a. bank account). Payment by bankcards also transfers the risk of a fraudulent transaction from the payee to the card-issuing bank, but only in those cases where the physical card is used as part of the authorization of the transaction. Payment by bankcard leaves the risk of fraudulent transactions with the payee if, as is inevitable in an Internet or telephone transaction, the physical card is not presented as part of the authorization.

Transactions that are mediated by computer also offer opportunities for imposters posing as legitimate merchants. Maximum reduction in the risk of fraudulent transactions of all types requires multi-factor and multi-channel authentication.

In those cases where the card-issuing bank bears the risk of fraud, it charges the payee a fee to compensate for that risk. In those cases where the payee retains the risk of fraud, the payee incurs the costs of unauthorized transactions directly. Whether directly or indirectly, payees bear the cost of unauthorized transactions. This cost in turn is built into the cost of goods sold and services rendered to the public. It is called, hereinafter, the "interchange fee."

Thus, although the public is protected by law from directly bearing the losses on most fraudulent transactions, eventually it pays indirectly for all the losses from unauthorized transactions. Moreover, the public pays even more than the losses themselves: first, the public bears significant costs from fraud and identity theft in time, inconvenience and temporary loss of the use of funds. Second, the public indirectly bears the significant costs incurred by banks, merchants and their insurers to mitigate risk. A processing fee is charged to the payee to cover both the processing costs and risk to the bank or non-bank financial institution that serves the payer. This fee has become the subject of controversy as bankcard transaction processing fees have risen steadily despite gains in fraud mitigation technologies, including new and additional factors to authenticate payment authorizations and economies of scale. Banks have come to rely on this source of non-interest income, especially in this age of dubious assets on balance sheets due to previously lax lending practices. Recent Federal Legislation has reined in what merchants regard as runaway interchange fees. This legislation also protects the consumer with a mandate of notification messages to accountholders when a 'good funds' balance or a credit limit may be too low to support automatic debit of a particular payment.

An argument can be made that today's bankcard industry is effectively unopposed by alternative payment systems of any size or significance. The bankcard interchange fee merchants pay is passed on in everyday prices. It is essentially a hidden tax on everything we purchase.

The interchange fee is split among the participants in the payment value chain and has been heretofore regarded as an inherent element in any new payment ecosystem. Led by the dominant bankcard companies, merchants and banks alike believe that any new payment method must run across 'existing rails' or payment networks to minimize cost related to conversion. The so-called interchange fee is the by-product of a system of payments that is prevalent today.

In these payment systems, the cardholder agrees by signing the bankcard application contract to permit the merchant that obtains his card number to have the cardholder's implicit permission to have the merchant's bank send an automatic debit transaction instruction to the payer's bank for the automatic debiting of his credit or demand deposit account.

Such systems, based on implicit permission, were developed in an age before there were smart phones and a truly ambient Internet. Smartphones, because of their ubiquitous connectivity, are an increasingly popular choice to provide an extra authentication channel and factor to insure that the risk surrounding the payment is minimized. Furthermore, this 'additional rail' or communication network can be used to send explicit permissions on a transaction-by-transaction basis or to modify one's a priori permissions policy for an entire class of transaction types.

The smartphone is rapidly becoming the platform of choice to manage a range of applications involving the transfer of monetary or informational assets. It has become the consumer's hub for vendor relationship management. Mobile device users choose among thousands of smartphone based applications. It is a common practice among applications developers to layer application functions on other applications. Hotels and restaurants deploying Google Maps on their reservations web sites are classic examples of this phenomenon. Such vertical integration is successful because it improves the user experience. Users shun applications that require too many steps or decisions to attain basic goals.

Knowing the true identity of the other party is the best predictor of a successful transaction. However, we are too fearful or simply don't know how to pay electronically, especially when concerns about privacy often prevail. When we must make emergency, last minute or just spontaneous electronic payments, we pay exorbitant fees or we pay a 'hidden tax' (interchange fee) that is built into everyday prices. What is needed is a convenient, private, and safe way to send and receive money instantly, anywhere, anytime with added benefits of tailored analyses of our transactional 'bread crumbs.' These 'bread crumbs' of information are potentially valuable enough that consumers may choose to divulge their identity information to processing systems in order to receive tangible benefits such as coupons, rebates and the like. A mechanism for the wishes of consumers to be established once, for several different kinds of transactions, eliminates the tedium of too many steps or permission decisions to divulge identity information. A system to determine a priori when permissions are explicitly given and when permissions must be obtained from customers in real-time is the subject of this invention. The term customers, in this application, may include entities, individual people, and, in some embodiments, agents of the customers.

This extra communication channel of the smartphone substantially reduces risk of fraud and associated processing costs in the bankcard industry. As there is downward pressure now on interchange rates, new business models have arisen where the consumer can be presented with an electronic invoice or bill, directly to his smartphone, and with which he can explicitly authorize a payment be pushed to the merchant's account. Modigliani, U.S. patent application Ser. No. 10/786,023, published Feb. 12, 2004, teaches synchronization of unique identifiers associated with payments at different institutions. It is a Method and System for obtaining a routable instant or next-day payment address as well as other informational attributes that are associated with unique identifiers that can be discovered and trusted to be true. Modigliani teaches that payments (and bill presentments) made to such properly constructed and registered payment addresses can be made without risk of repudiation due to lack of explicit authorization.

In other words, when an explicit permission to push a payment to the payee is given, a receiving bank can justify posting good funds to an account in advance of actual settlement because it is knows that the transfer will not be reversed by the sending institution for any reason.

Furthermore, by making a registry of such payment addresses publicly available, the risk that the payment address (as well as other informational attributes associated with the unique identifiers) is unknowable and/or not certified to be authentic is eliminated. When payees' unique identifiers and associated information attributes are registered in the directory/processor taught by Modigliani, '023, the risk bearer's costs from the prevalent implicit-permission-to-automatically-debit method can approach zero.

The risk of the transaction is borne entirely by the payer, who explicitly authorizes the payment, not their bank. The payee's electronic payment address and associated information attributes such as but not limited to name, physical address and phone number, are guaranteed to be true by the registrar that supplies the asset transfer address to the validation registry. In the unlikely case that the registrar bank has been tricked by a fraudulent customer impersonating a legitimate payee, it (i.e., the registrar bank) would be responsible for any transaction failure attributed to an inaccurate payment address. Further, when a payor's unique identifiers and associated information attributes are also in the registry, the payee's system can query and react according to preset instructions. Hill, U.S. Pat. No. 7,349,843 teaches a system assigned unique identifier is placed on the outgoing mail. Tsuei, U.S. Pat. No. 7,213,748 describes a privacy protection scheme in which the user is assigned a private code identifier that is placed on the letter or package. The delivery service, but not the sender, has access to a database that can convert the privacy code into the recipient's actual address. In this way, a consumer can have goods shipped to his privacy code, and the shipper will reliable the item with consumer's address, so that the consumer's identity or location need not be revealed to the merchant who sends the goods. Instructions can pertain to various kinds of information as well as various kinds of application contexts. Logan, U.S. patent application Ser. No. 11/198,124, published Nov. 24, 2005 teaches that user-chosen vanity names or existing identifiers already assigned to the user, such a phone or fax number, URL, email address, or a Global Location Code can be cross-referenced in a directory and resolved to a physical address. A registry such as the one envisioned by Modigliani '023 does not need to presume which kind of unique identifier is easy to remember by a given user. A system is needed that enables users to determine, in advance, which unique identifiers (and permissions) relate to specific monetary asset transfer and/or informational asset transfer applications.

Now, payment systems are emerging where the merchant pays for the transaction processing and risk-bearer's cost by itself supplying information pertaining to the transaction instead of paying the traditional interchange fee. This flow of personal shopping behavioral data may be regarded as confidential by some consumers but in fact, the merchant owns this data and he can do whatever he wants to do with that information. If the merchant desires to reduce the payment processing burden of paying interchange with an implicit-permission payment system (such as debit or credit cards) by supplying sales data pertaining to each item purchased in a particular transaction, he can do so. If the merchant desires to reduce the burden of paying interchange by allowing a payment method that partially masks the consumer's specific identity while divulging such information such as mobile phone number or address of the consumer, he can do that. Personal identifiers add value to the many streams of data pertaining to transactions for data mining.

But in the bankcard era, when consumers gave card numbers to merchants along with their implicit permission to automatically debit their accounts, they did so with the belief that the merchants would never disclose their private shopping habits to others. However, nothing in the past prohibited merchants from selling their summary store sales data to large repositories. While Hill '843, Tsuei '748 and Logan '124 attempt to solve the problem of customer information such as delivery address becoming widely distributed by merchants among numerous data repositories, none of this prior art attempts the same for addresses for 'to and from' delivery of digital content much less delivery of monetary assets to so-called electronic payment addresses. As data repositories grew to oceanic proportions, inferential analysis has become the norm. Retailers and manufacturers alike seek direct referential knowledge of an individual's behavioral data segmented by their membership in one or many consumer groupings. What is needed is a mechanism that gives consumers the capability to regulate when and how their consumption data is used for analytical purposes so that unauthorized use of data analysis does not harm them in any way.

In brief, the old way of payments is based on implicit debits and the new way uses explicit permissions to "push" asset transfers (i.e., this is the explicit authorization taught by Modigliani '023). Just so, the emerging cases and systems where merchants use consumer information to "pay" for costs are based on implicit permissions to "push" these information transfers. This invention brings preset policy concerning when to allow, via explicit permissions, automatic information stores/transfers and when to require real-time customer authorizations to such information transfers.

This invention helps merchants by reducing systemic chargebacks associated with payments that are repudiated due to lack of proper authorization. Merchants offset their costs of acquiring valuable marketing behavioral analytics that are otherwise unobtainable by reducing or eliminating their interchange fees altogether. Merchants that elect to obtain analyses of their customers' behavior will have trade advantages in the marketplace because they will have new awareness and capability to communicate with their segmented customer base.

What is needed is a mechanism that replaces the current default condition of blanket implicit permissions with explicit permission whenever conditions arise whereby such is desired, and to do so without forcing a specific decision step for every transaction. The convenience of bankcards continues to be the standard by which all alternative payment methods are measured. Allowing one's 'transactional breadcrumbs' to be aggregated, sorted and mined can be valuable to consumers when merchants wish to offer incentives to return to the store for loyalty benefits such as special sale prices, rebates, and the like. Payments data is now more valuable than ever before for behavioral targeting. Online advertising/data analytic companies realize premium value for data related to payments, especially data from consumers when they transact while mobile. Online advertising/data analytic companies realize opportunities for mashups by consolidating reporting and giving advertisers the ability to compare data directly vs. trying to process it all themselves.

For example: when you order food online, you become part of a vast database that lenders might tap to help them determine whether you are a good risk. A food delivery proves that you actually reside at an address where you claim to be living. Moreover, all sorts of these data reservoirs exist, and none of them is off limits to lenders, who are coming off the worst financial debacle since the Great Depression. Risk management companies work with lenders and investors to build better underwriting mousetraps by continuously probing for ways to help clients quantify their risk to prevent fraud and otherwise insure the quality of their loans.

For example, they might peek into your online-buying habits. Someone who purchases his shirts from a Brooks Brothers catalog may have more disposable income than someone who shops at J.C. Penney. The safest lenders are digging into databases maintained by Domino's Pizza, Papa John's or Victoria's Secret. The only boundary is whether the information can be accessed legally. Mobile payments initiated from a smartphone can replace cash, checks and even bankcards for smaller transactions. Personal identifying information such as caller ID number & other identifiers may be used to authenticate the owner of the smartphone in order to mitigate risk that a payment is authorized. Trust that sales data obtained from authentic sources can be proven and legally certifiable will be valuable when dispute of information ownership may arise.

Some consumers care a great deal about privacy. Others recognize that in today's noisy digital world, privacy is hard, if not impossible, to protect, and they simply don't care to be stressed about it. Other groups don't mind having their shopping behavioral data aggregated by marketing cohort group, and if it only means that a phone number or address is needed to assign membership in one of several cohort groups then that is fine. As long as these consumers receive something of value in return, they are happy to leave behind a trail of 'digital breadcrumbs.' Still others may be reluctant to participate when they are uncertain about having to provide certain data, or how that data may be used, and may in fact provide misleading or false data to protect their privacy while participating.

In today's world, many kinds of information now flow into repositories that may be owned or operated by entities other than the original merchant. In many cases, these repositories, having acquired the ownership of or access to such data, are not restricted on their use of such data. In Modigliani '023, the interaction (query/response/transact) with the registry results in an asset transfer without repudiation from lack of authorization. When information attributes (permissions) are supplied when the registry is queried by a merchant (e.g. to send a bill listing items ordered for a meal after a menu selection is made), the subsequent compilation of sales data in a repository specified by information attributes (permissions) can also be said to be certifiably obtained. This adds value because of the assurances of provenance and quality of the data.

This phenomenon will increase in likelihood as non-repudiable electronic payments become more prevalent and consequently increase the volume and value of transactional data. Some project that the value of data to payment processors and banks will soon exceed the value of the income from interchange.

Many consumers are flustered and feel overwhelmed by the cacophony of digital noise in modern life. Asking a consumer to provide explicit permission to allow information flows for each transaction is unrealistic and burdensome. What is needed is a system and method that enables the consumer to establish and lock down his own custom rule-set for a priori permissions pertaining to defined categories of information flows that result from transfers of both monetary and/or informational assets. Such a system supports the range from default conditions when implicit permissions are granted to default conditions when explicit permissions need to be granted. A number of responses to this set of problems have been proposed.

Mohsenzadeh, U.S. Pat. No. 7,742,884 issued Jun. 22, 2010 is for a Method and System for conducting payment transactions over the public telephone network. In Mohsenzadeh, when goods or services are purchased from a merchant, an individual can initiate, authenticate and authorize a payment during a single phone call. This method stores the number of the telephone device in the payment processor's system for retrieval and match with caller ID information as a factor of authenticating the owner of an account is the same as the owner of a telephone device. In Mohsenzadeh '884, when the payer authorizes the transaction with multiple authentication factors such as a PIN, Caller ID and even other authentication factors, things proceed somewhat similarly to how they would with a traditional credit or debit card transaction, i.e., implicit permission is presumed and an automatic debit of the payers account ensues. Normal interchange fees are still assessed. There is no mechanism proposed to operate to ensure a priori policy requiring explicit permission of the purported authorizing party regarding the disposition of discreet data pertaining to what was purchased in the transaction. While Mohsenzadeh '884 teaches how additional authentication factors can reduce risk of repudiation with a simple user experience, he relies on the unique identifier of the phone number associated with static bankcard or bank account numbers. Consequent automatic debiting once said numbers are presented alongside multiple factors still supports traditional interchange economic models and NOT a model that acquires information in lieu of interchange or the lowering of interchange costs by some measure of value derived from the acquisition of information.

Monaghan, United States Patent Publication No. US2004/0030645, published Feb. 12, 2004, is for a Method and System for Performing a Transaction Utilizing a Thin Payment Network. In Monaghan, when goods or services are purchased from a merchant, the purchaser provides identification to the merchant. The merchant then forwards the purchase details to a processing means that verifies the merchant's authenticity and forwards the transaction details to the purported purchaser's bank. The bank issues a request through a separate channel to its customer, who purportedly is the purchaser, for authorization using a PIN. If the bank receives the correct PIN, the bank authorizes the transaction, and things proceed somewhat similarly to how they would with a traditional credit or debit card transaction.

Monaghan teaches that the current methods of authorization are not effective because such methods only confirm the presence of funds in an account and fail to address the issue of improper authorization of the user involved in the transaction. Ultimately, upon receipt of a periodic statement or even sooner, a user may dispute a monetary transaction on the grounds of improper authorization, and if successful, either the payee or the bank suffers a loss. Another issue recognized by Monaghan with regard to current processing methods is that sensitive information is available to numerous parties, who may misuse it or fail to protect it from identity thieves. When information pertaining to a person's personal behavioural characteristics is gathered and sold, there is further risk that a user may dispute an informational transfer transaction on the grounds of improper authorization, and if successful, either the entity receiving and/or purchasing the information or the entity sending and/or selling the information suffers a loss.

Both Monaghan and Mohsenzadeh, like the current PIN debit system, rely on PINs (or passwords) as their primary security mechanisms. But a PIN (or password) is not a very robust authorization factor: for example if a person writes a PIN down to avoid forgetting it, the PIN is subject to compromise. The act of knowing what a PIN or password conveys an implicit permission to present it for authorization.

What is needed is an invention that addresses PIN/password and other factors such as callerID weaknesses by implementing explicit permissions in a fashion analogous to Modigliani '023's explicit authorizations to pay a deposit-only payment address without repudiation due to lack of authorization.

In Monaghan's second patent application, U.S. Patent Application Ser. No. 61/366,029, of Jul. 23, 2010, advances the art beyond the earlier system described in the '645 publication which is now public domain material since that case was abandoned. The original '645 publication discloses a process flow that enables an invoice to be routed to the consumer's financial institution which in turn, contacts the consumer to seek approval and authentication from the consumer for the purchase of the goods or service by entering a password or PIN to indicate that the consumer's approval of the transaction. The consumer's financial institution then sends a message to system indicating approval. The system then acknowledges this approval to the merchant who then releases the goods or service to the consumer. The payments may be pushed via efficient ACH networks, eliminating the need to pay higher interchange fees that are split among each participant in the payment ecosystem.

The Monaghan '029 application teaches how the one time code supplied by a financial institution replaces all personal identifying information of the payer. Consequently, the transaction database of the merchant will contain the one time code as a unique identifier only for that transaction. This renders all consequent data pertaining to the transaction to be assigned to an anonymous payer. Merchants and manufacturers alike place higher value on behavioural analytics segmented by marketing cohort groups. Such segmentation can only be deduced when the phone number or address of the consumer is assigned to the transactional data from the purchase event. The invoice details associated with any one time code may still be presented to the consumer prior to the payment being approved so that the consumer can authorize payment. This method simultaneously: a.) enables the consumer's bank to obtain an aggregation of invoice details for monetization from data-mining without the consumer's explicit permission; and b.) avoids needing consumers' explicit permissions for non-banks to exploit data pertaining to the consumer's shopping behavior because the user identity is never retained by the merchant or the payment system.

However, neither Monaghan system proposes an operational mechanism to ensure a priori policy requiring explicit permission of the purported authorizing party regarding the disposition of discreet data pertaining to what was purchased in the transaction. The sales data of the consumer is still retained by the payer's bank and no mechanism is proposed to set a priori policy instructions to exploit or safeguard these 'transactional breadcrumbs' according to the consumers' wishes. This remains an unfulfilled need.

Singhal, U.S. Patent Publication No. 2002/0062281, published May 23, 2002, discloses a payment system in which a user may make a private and secure payment to a merchant using a wireless device, a payment card or a bank card or to another party using a wireless device. Singhal '281 proposes a payment system in which the user does not share his financial information with, and may not even disclose his identity to, the merchant and does not disclose to the user's bank the type of purchase involved (thereby keeping confidential from both the user's bank and the merchant the user's purchasing habits). Further, the user does not have to carry his bankcards or checks. In each embodiment in which a payment is transacted to a merchant, the payment system includes, generally, a central system that works in conjunction with a wireless device belonging to a user, a payment card generated by the central system or an existing bank card. The payment card bears no relationship to the banking entity or the existing bankcard, but it may be utilized to identify the user in the transaction.

In practice, a user selects merchandise or services for purchase from the merchant. The user scans or enters transaction related information into a wireless device and enters either a PIN or a pre-stored number identifying a payment card or a bank account that the user is authorized to access. The wireless device is used to create a payment request that is transferred to the Singhal payment system for authorization. The central system assembles a payment record including pre-stored bank account data and submits the information to an automated clearinghouse. The Singhal system proposes no additional means to ensure explicit permissions of the purported authorizing party regarding the disposition of discreet data pertaining to either a monetary or informational asset transfer event.

Holcombe, U.S. Pat. No. 6,671,696 and U.S. Pat. No. 7,136,869 disclose an Informational object authoring and distribution system and a Common point authoring system for tracking and authenticating objects in a distribution chain, respectively. These patents rely upon a registry to track uniquely identified products but neither envisioned a system and method for a priori policy granting explicit permission to certifiably attach and store metadata that commemorates the transfer of ownership of an informational asset from one party to another party.

Monaghan, U.S. Provisional Patent Application Ser. No. 61/377,362 filed on Aug. 26, 2010 discloses a map of rules that accompanies money to control how it is spent. This patent relies upon a registry to manage money under an entire new definition of money. Monetary assets are tagged with metadata or rules that restrict its use. Monaghan '362 does not give users a method to assert ownership privileges or restrictions over assets of an informational nature.

As more and more goods and services reside 'in the cloud' and as more and more data about physical goods and services reside in the cloud, the ability to transfer and later track rightful ownership along with certified digital provenance documentation becomes increasingly valuable.

SUMMARY OF THE INVENTION

This invention relates to a computer system and method to a.) grant explicit permission for transfer, storage and retrieval of various kinds of cloud-based information; b.) establish ownership of cloud-based information; c.) maintain safeguards to ensure that custodians of cloud-based information enforce privacy preferences of owners and d.) ensure that cloud-based information being viewed is related to the individual consumer or entity identified as being associated with the information.

One example would be information pertaining to transactions, such as data describing goods sold by the transfer of monetary assets. Another example would be digital objects associated with the transfer of information assets. Yet another example would be information pertaining to services rendered such as calories consumed in a meal served at a restaurant.

Since this cloud-based information may also include additional information related to identity, authentication, authorization, and preferences, this invention optionally includes a.) having an agent act on behalf of the subject of the information; b.) having an agent act on behalf of the requestor of the information; and c.) having ownership privileges, privacy preferences, and/or notification preferences be handled as cloud-based information subject to ownership and safeguards.

Aspects of the present invention seek to overcome some of the shortcomings of the prior art. For example in Mohsenzadeh's '884 patent, the disclosure overcomes the limitations of relying on just a PIN factor to authorize a payment by matching the caller ID of the mobile device with a pre-registered value. However, in every embodiment of the '884 invention, the transaction platform relies on bankcard networks or ACH networks to process payments and performs no function to gain and store more information relating to a point of sale transaction—such as bar code data—than is ordinarily provided to a consumer. Also, caller ID is implicit and may not be secure.

For another example, in Monaghan's later '029 publication, the disclosure overcomes these limitations of '645 by ensuring privacy by not requiring any private or identifiable information of the consumer to be supplied. Furthermore, in every embodiment of the '029 invention, the transaction platform gains and stores electronically, more information relating to an anonymous point of sale transaction—such as bar code data—than is ordinarily provided to a consumer.

However, this information is stored only in an anonymous form, and thus only consumers can query this information anonymously via a unique transaction identifier. Without a system whereby the payer configures a policy-driven mechanism that grants explicit permissions (or requires permissions to be obtained in real-time) to record and transfer transaction information, consumers miss out on the opportunity to receive valuable coupons, offers of interest, rebates and the like. The present invention provides such a policy-driven mechanism, and accordingly, is able to use consumer transaction information more effectively, by linking the information to specific consumers. In one embodiment, this transaction information could be grouped or aggregated by marketing demographic types.

This transaction information could, for instance, allow merchants to target their promotions or advertisements to specific customers. For example, a new food delivery restaurant may want to target consumers who are known to order delivery food, and may provide coupons as incentive to these customers. Alternatively, a food delivery restaurant may wish to target customers who do not currently order delivery food.

In Singhal's '281 publication, the disclosure overcomes the problem of providing static account numbers to merchants by pre-registering bankcard data in an intermediary processing system. However, this, too, does not addresses the issues related to implicit permissions.

In Holcombe's '696 and '869 patents, neither discloses a method for transferring and assigning informational objects to certifiably commemorate the transfer of ownership rights of information derived from asset transfer transactions.

In solving the above problems and providing the above solutions, certain embodiments of the invention have been developed to facilitate the a.) institution of permission preferences pertaining to the release of personal identifiable information; b.) automation of conveying those preferences to merchants, processors and repository institutions; and c.) a legally traceable chain of evidence to the source of the permissions and assertions of ownership rights to cloud based information.

In additional embodiments, agents may be acting on behalf of the subject of the cloud-based information or on behalf of the requestor of the information. In one embodiment, a subject may grant ownership rights, privacy preferences, and notification preferences to another individual entity with a custodial relationship or with a Power of Attorney. For example, a responsible individual could be designated to act for an infirm person or for a minor.

In another such embodiment, a requestor could authorize an agent to act on its behalf when requesting a transfer of information assets, given that the subject of such information authorized the use of such agents. For example, a customer seeking to enroll with a brokerage could allow it to authorize a credit reporting agency to, on behalf of the brokerage only, make information transfer requests that are related to the customer.

The system may effectuate the functions of:
presenting which types of information could require explicit permission for release,
presenting case examples so a priori permission preferences become rules,
adding new rules attributes to the registry,
supporting automatic conveyance of rules to payment systems which may need instruction to direct sales data to repositories, and
supporting automatic conveyance of rules to payment systems which may need instruction to retrieve sales data from repositories.

In a preferred embodiment, the preceding steps are added to the registrar accreditation process and lookup process disclosed in O'Brien, U.S. patent application Ser. No. 11/592,510. In addition to banks certifying their State Banking and Federal banking license is current, a new function establishes and conveys preset instructions for information delivery. The information and instructions can be relevant to particular communities of interest and/or every registrant in the registry. For the illustrative example of a customer purchasing and paying for goods or services, the following lists indicate categorical ranges for types of cloud-based information and scope of pre-setting of permission rules.

List of Types (or Categories) of Information:
PII (Personally Identifiable Information) (e.g., name, driver's license number)
Partial PII (identifies marketing cohort group affiliation e.g. address, mobile number)
Other Demographic Information (e.g., age, gender, ZIP code)
Purchased Items Information (e.g., SKU, RFID, price, quantity)
Transaction-specific Information (e.g., payment method, date and time of purchase)
Agent Identifications (e.g., someone authorized to act on behalf of another)
Other data and metadata List of Scope (or Categories) of Permission Rules
Ownership of data items or types (e.g., customer, merchant, registry)
Masking of data items or types (e.g., removing or randomizing PII)
Aggregation of data (e.g., using demographic or other groupings)
Data access permissions (e.g., who can access what data under what conditions)
Data storage permissions (e.g., who can store what data under what conditions)
Notification preferences (e.g., rules for pre-set or event-driven notifications)
Data lifetimes (e.g., how long data items or types may be accessed or stored)
Agent authorizations (e.g., when an authorized agent can act on behalf of a customer or requestor)

Logical decision-making combining type and scope of information and permissions may require too much thought for mobile users to process when they are mobile. While some users may always disregard privacy concerns and others may always wish to keep their personally identifiable information private, the objective of the present invention is to serve all users, including those who wish to distinguish when and how their permission to release PII, Partial PII or Other Demographic Information is given. It is a further objective of the invention to present the range of possible permission rules to users so they can thoughtfully select rules that govern when permission to release various information are to be given to merchants, payment processors, information repositories and the like. It is a further objective of the invention to register said (selected) rules in, or to have said (selected) rules linked to, a registry of unique identifiers and payment addresses vouched for by accredited registrars in a registry of unique identifiers & payment addresses. This enables entities that need to know said rules to obtain necessary permissions so that information may be sent to various repositories tagged with the corresponding level of Identifiable Information permitted by the user (i.e., customer) for a particular application context.

Said rules may be defined and assigned at the point of enrollment when the registrant's unique identifier is linked to a payment address. Said rules may be added to a registry after the initial enrollment event. O'Brien, U.S. patent application Ser. No. 11/592,510 discloses a system and method for various communities of interest to extend the range of identifier types that are linked to the unique identifiers in the root directory of a network of synchronized registries to support asset transfer applications of a non-monetary nature. It is a further objective of the invention that 'said rules' can be similarly added to the registry as linked attributes whenever an accredited registrar sponsors new attribute(s) to the network of registries that enable(s) new information asset transfer applications.

The following is a partial listing of examples of new attributes to the network of registries disclosed by Modigliani '023:
What information for which masked ownership would be asserted (e.g. when a consumer is to be identified only as a member of a marketing cohort group, not as an individual)
Where to store that information if it is asserted to be owned exclusively by an individual requiring access with explicit permission only
Whether information ownership is of a non-exclusive nature and access is to be restricted
Whether information ownership is of a non-exclusive nature and access is to be unrestricted.

DETAILED DESCRIPTION OF THE INVENTION AND ILLUSTRATIVE EMBODIMENTS THEREOF

The present invention relates to establishing and using a network of registries of unique identifiers linked to payment addresses, privacy permissions, and notification preferences. In a preferred embodiment of the present invention, a central directory and/or processor is established and made available to entities wishing to aggregate assigned ownership of cloud-based information and make such available for retrieval by owners. When a payer wishes to pay in a manner that allows for the aggregation of his sales data to a cloud-based repository or to an application residing on his computer or smartphone, the central directory can act essentially as the definitive root directory to all forms of user permissions and preferences. According to one embodiment, directory listings can become activated and public only after banks or other payment destination entities complete a formal enrollment process, which registers account, linkage information and user preferences pertaining to permissions to release his personal identity information.

Figure 1:
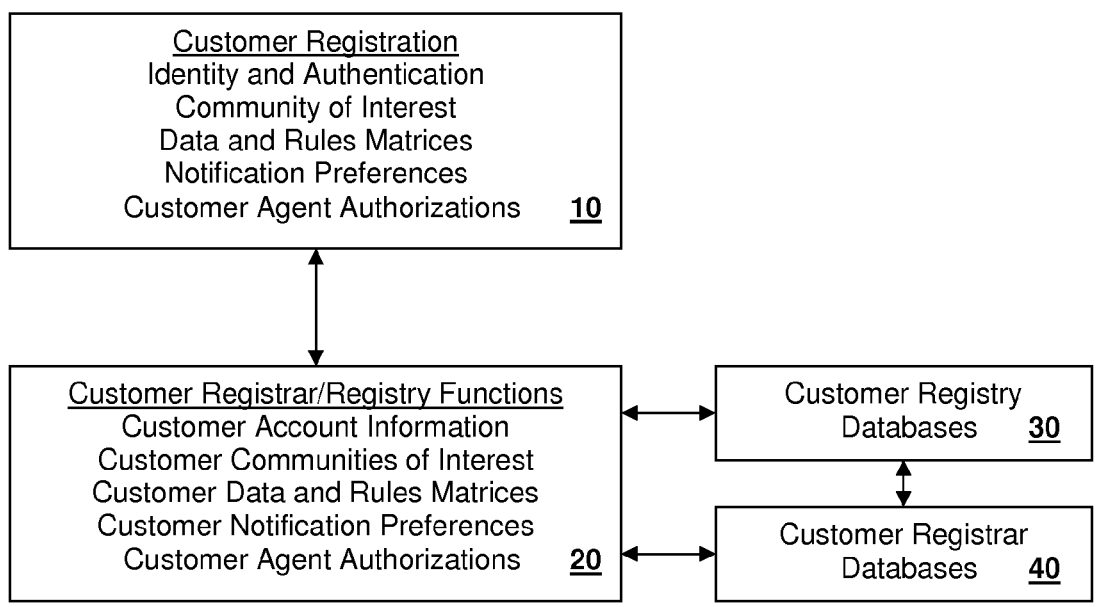
FIG. 1 depicts a diagram of the method and system of establishing customer Registrations of Explicit Permission Rules, according to an exemplary embodiment of the present invention.

In FIG. 1, customer registration 10 may be created or modified by a customer accessing the Customer Registry/Registrar Function 20. Typically, the customer who is registering will interact with the Registrar, first by establishing identity and then by authenticating. Then the customer and the Registrar will interact as the customer enters or updates information such as Community of Interest (e.g., shopping, health care), Data and Rules Matrices (which may be general and/or relevant to specific communities of interest), and Notification Preferences (how and under what conditions the consumer chooses to be notified when information is requested). Typically, also, the Registry/Registrar function handles the updating of Customer Registry databases 30 from Customer Registrar databases 40. Finally, customer registration may include the authorization of one or more agents to act on the customer's behalf.

Figure 2:
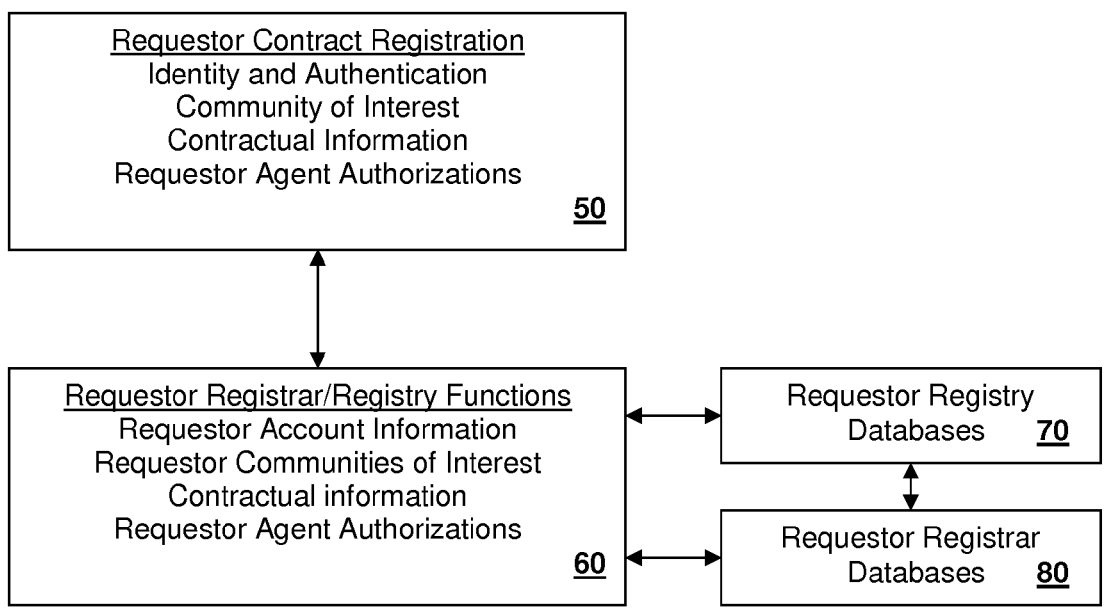
FIG. 2 depicts a diagram of the method and system of establishing requestor Contracts for use of Explicit Permission Rules, according to an exemplary embodiment of the present invention.

In FIG. 2, requestor contract registration 50 may be created or modified by a requestor accessing the Requestor Registry/Registrar Function 60. Typically, the requestor who is registering will interact with the Registrar, first by establishing identity and then by authenticating. Then the requestor and the registrar will interact as the requestor enters or updates information such as Community of Interest and Contractual Information. In addition, the requestor may authorize one or more agents to act on its behalf. Typically, also, the Requestor Registry/Registrar function handles the updating of Requestor Registry databases 70 from Requestor Registrar databases 80.

Depending on communities of interest, embodiments, or implementations, different databases may or may not be combined or co-resident. In one alternative, customer Registry and Registrar databases may be owned, operated, or combined by the same entity or entities. In another alternative, customer Registry and requestor Registry databases may be owned, operated, or combined by the same entity or entities. These databases and their corresponding functions may also be implemented and operated in a distributed fashion.

Figure 3:
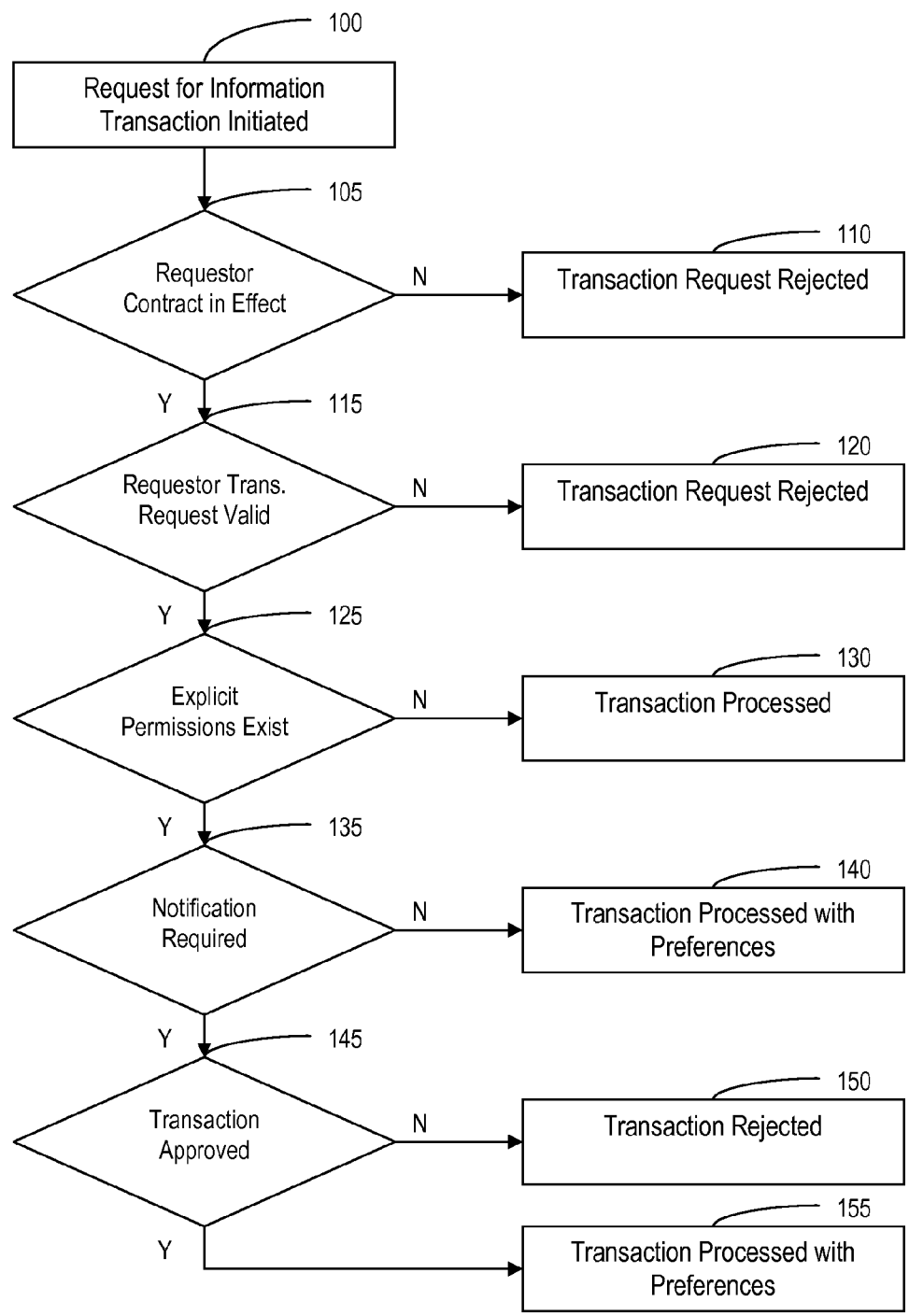
FIG. 3 depicts a flowchart of the method of using the information transaction Explicit Permission Rules, according to an exemplary embodiment of the present invention.

In FIG. 3, an information transfer request is initiated 100. This request may be initiated directly by a requestor, indirectly as part of a related transaction, or on the requestor's behalf by an intermediate or associated party or agent. If a contract does not exist for the requestor as in 105, then the request is denied as in 110. If the contract does exist, then the validity of the request is ascertained as in 115. If the information request is not valid, then the request is denied as in 120.

If the request is valid, then a check is made as in 125 to see if explicit permissions are required for the subjects (e.g., customers) of the request. If no explicit permissions are required, then the transaction is processed as in 130. If explicit permissions are required, then a check is made as in 135 to see if notifications are required. If no notifications are required, then the transaction is processed as in 140 using the preferences indicated by the explicit permissions applicable to the requestor and the subjects of the request.

If notification to approve the request as in 145 should fail, for example by timeout of the response or denial of the request, then the transaction itself is rejected as in 150. If the notification response is to approve the request, then the transaction is processed as in 155 using the preferences indicated by the explicit permissions applicable to the requestor and the subjects of the request.

Typically, the decisions made in 105 and 115 relate to the requestor and accordingly may be based on information contained in Requestor Registry databases 70. Typically, also, the decisions made in 125 and 135 relate to the customer and accordingly may be based on information contained in Customer Registry databases 30.

Figure 4:
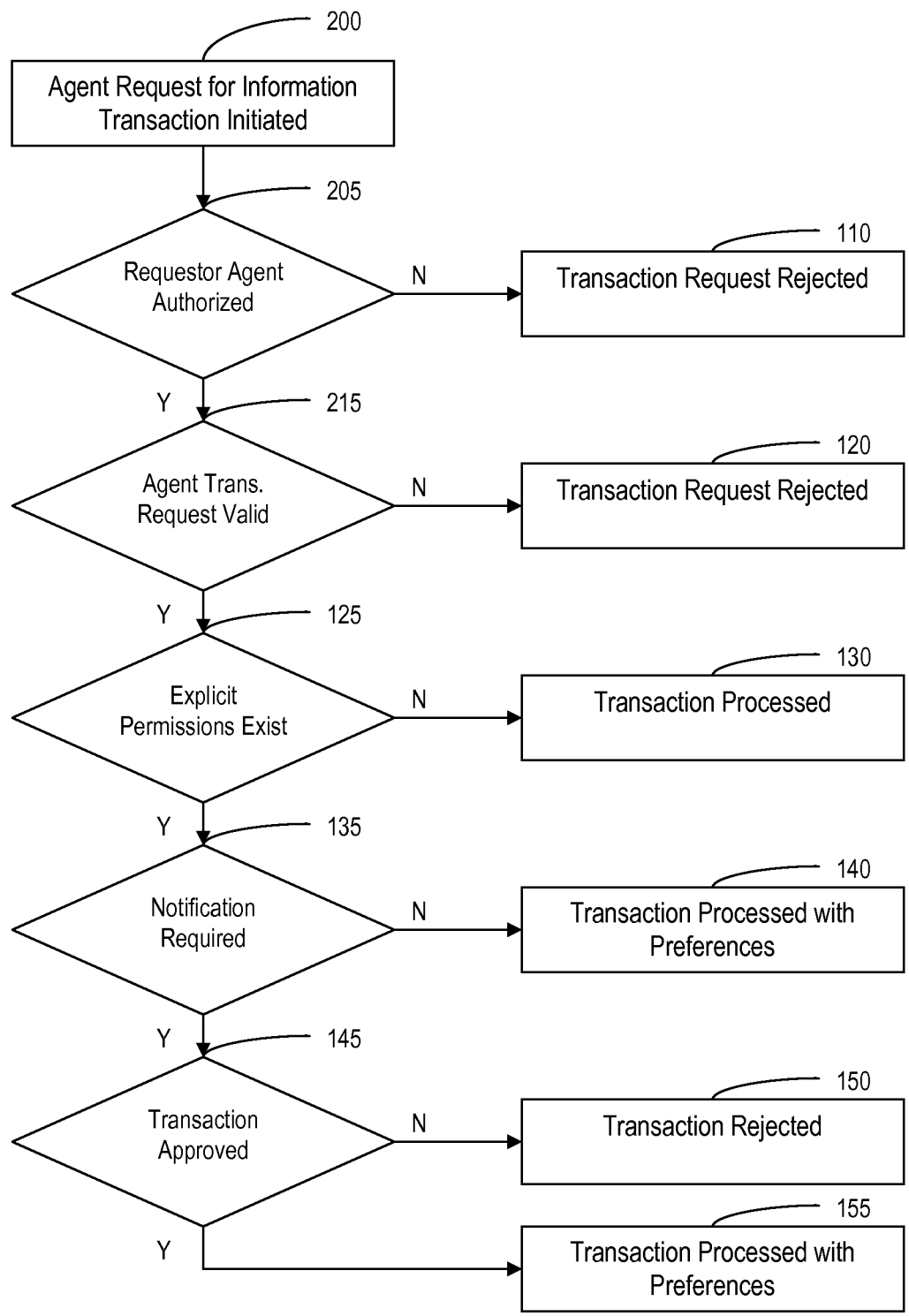
FIG. 4 depicts a flowchart of the method of using the information transaction Explicit Permission Rules for an agent acting on behalf of a requestor, according to an exemplary embodiment of the present invention.

In FIG. 4, an information transfer request is initiated by an agent 200. This agent is acting on the requestor's behalf. If authorization for this does not exist as in 205, then the request is denied as in 110. If authorization does exist, then the validity of the agent's request is ascertained as in 215. The remainder of this flow is identical with that in FIG. 3. Note that requestor authorization of an agent is a function of the requestor contract registration process as shown in FIG. 2.

Figure 5:
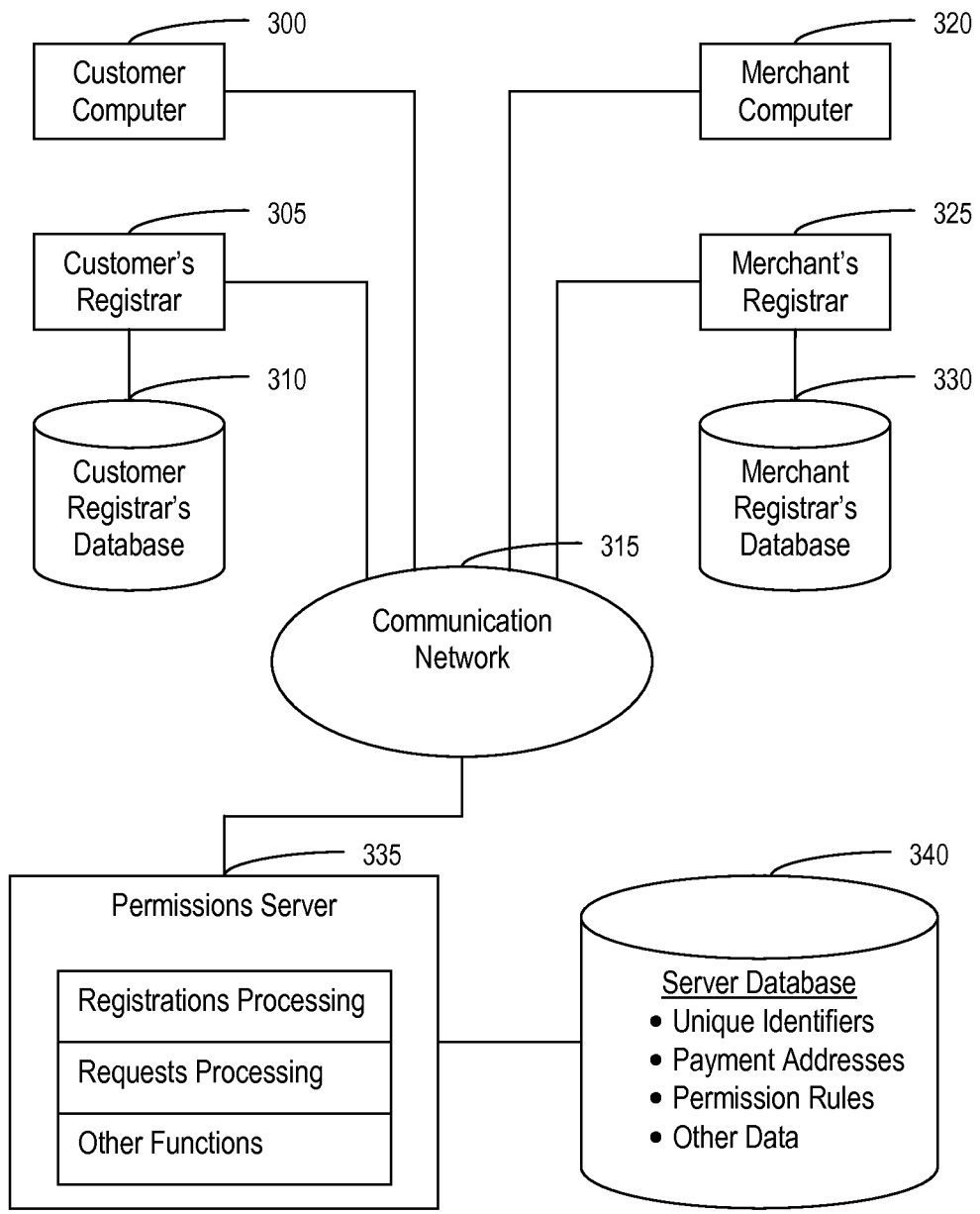
FIG. 5 depicts a diagram of a system wherein customer registrations and merchant registrations are stored in a Permissions Server, according to an exemplary embodiment of the present invention.

In FIG. 5, a customer's computer 300 is used to initiate registration with the customer's registrar 305, which stores the registered information in its (customer registrar's) database 310. The customer's computer communicates with the customer's registrar via a communications network 315. This network could consist of a combination of networks, for example, where the customer uses broadband access via a service provider, the registrar uses broadband access via another service provider, and the service provider networks communicate over the Internet or other network infrastructure.

The customer's registrar shares registration data with the permissions server 335, which stores registration data in its own database 340. The registrar communicates with the permissions server over a communications network 315. Processing of registrations is one set of functions of the permissions server, which also handles processing of transaction requests and other functions, such as other registry processing. The server database contains the registered data, including unique identifiers, payment addresses, permission rules, and other data.

There may be a number of different configurations or implementations; the one given here is illustrative.

A merchant's computer 320 may be used to register with the merchant's registrar 325 in order to update said registrar's database 330. In the embodiment described here, the merchant's registrar is distinct from the customer's registrar, but other embodiments could use other configurations, for example, with a common registrar. Again, a communications network is used for communications between the merchant's computer and the merchant's registrar. Likewise, a communications network is used to communicate between the merchant's registrar and the permissions server.

In the embodiment described here, the permissions server maintains a database which includes both customer and merchant data. In other embodiments, different parts of the database might be stored or managed in other configurations. Also, in other embodiments, there may be other processing architectures, such as a networked implementation of distributed permission servers. The embodiment described here is illustrative and not limiting.

Figure 6:
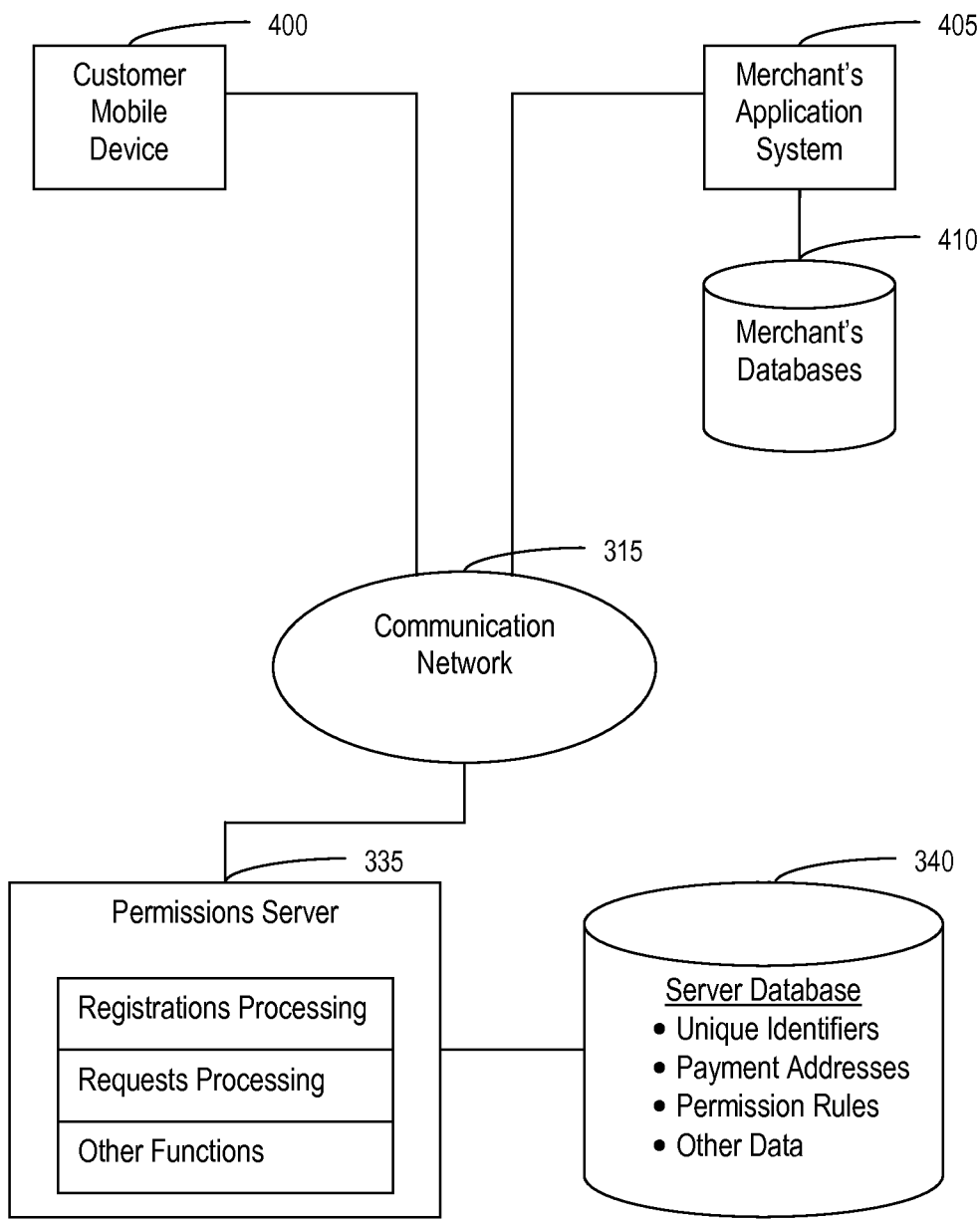
FIG. 6 depicts a diagram of a system wherein an information transfer request that entails customer notification and response is handled by a Permissions Service, according to an exemplary embodiment of the present invention.

In FIG. 6, a customer may use a mobile device 400 to make a purchase from a merchant's application system 405 via a communications network 315. In this example, the customer may be using a wireless network, the merchant may be using broadband provided a service provider, and the Internet or other network infrastructure may be used to provide overall network connectivity.

Depending on the merchant's application, including such information as may be stored in the merchant's databases 410, the merchant's application system may initiate an information transaction request to the permissions server 335 via the communications network. For example, the merchant's application might wish to share purchase information within a particular community of interest. The permissions server checks its database 340 and returns the stored explicit permission rules for the identified customer back to the merchant's application.

In this example, the customer may have a stored rule indicating that notification and confirmation are required as part of the overall customer interaction with the merchant. In that case, the merchant's application system will send a notification to the customer via the communications network, and the customer will send a confirmation back to the merchant's application system via the communications network. Once that has been received, the merchant's application system may continue with processing its requested information transaction. This information transaction was initiated by the merchant's system during processing of the customer's action to make a purchase. The use of permission rules ensures that the customer's data is handled appropriately.

Bill Presentment & Payment

Certain configurations of the invention may enable an owner of a payment account to establish permanent instructions for his financial institution regarding how to pay bills. For instance, when certain bills are delivered directly to an accountholder's payment address of said financial institution, said financial institution is to automatically pay the bill without needing the accountholder's explicit permission to do so.

Other configurations may enable an accountholder to be notified to give his explicit permission to release a payment for every bill. The registry can be used as a guide for financial institutions to follow with regard to bill pay. For instance, institutions can check the registry to obtain a consumer's explicit permissions to pay certain bills automatically when they are from billers earmarked as recurring billers. In other circumstances, the registry might instruct the financial institution that an explicit permission from a separate authorization step is needed to release a payment for a bill that is presented from a new and/or spontaneous biller. The information associated with both pending and paid bills may be automatically gathered and automatically stored in a third party repository and/or accounting software system again, with either explicit permissions or a requirement that real-time authorization from the customer be obtained before disposition (journaling, recording) of the bill.

Supply Chain

Certain configurations of the invention may require the issuer of a purchase order, Company A, to give his explicit permission before a company's supplier, Company B, could automatically obtain information from a third party information resource such as bank account balance and/or average balance history information. In this example, company B creates goods that are sold to company A, which processes them further or sells them to a distributor or end user. The volume and frequency of purchase orders change as economies expand or contract. It is a common practice to require freshened letters of credit for every new transaction. This costs Company A time and money to obtain. This is especially true if Company B has little if any historical knowledge of the credibility of Company A. Obtaining Company A's explicitly permitted released of financial credentials from a trusted repository that relays accurate, up-to-the-minute information speeds the procurement process, while lowering costs and risks for both transactional parties.

Health Care Information

Certain configurations of the invention may allow for control of or notification of access to a consumer's health care information. In a first example, an individual may pre-authorize, or give explicit permission to, various entities within a community of interest to access various types or views of health care data. Further, the individual may set notification preferences, for example, when an entity within a community of interest makes its first request for such an information transaction.

In another embodiment, the individual may authorize another individual to act on behalf of the first individual for all purposes related to the invention, including registration changes, privacy preferences, and notification preferences. For example, an aging individual may designate an adult child, e.g., via a Power of Attorney, to act on the individual's behalf once the individual becomes infirm and incapable, or undesirous, of carrying the burden of responsibility for dealing with health care matters, including controlling access to health care information.

Information Transaction Request Agents

Certain configurations of the invention may allow a registered requestor to authorize an agent to perform information transfer requests on its behalf. In a first example, an online merchant makes enrollment available to consumers. As part of that enrollment, the merchant may wish to verify the credit status of an enrollee. If, for example, the consumer has authorized the merchant to make such requests, and if the merchant has authorized an agent, such as a credit reporting agency, to make such a request on its behalf, then the agent may in fact perform the inquiry. In this case, the merchant would request the agent to verify the credit status of an enrollee, the agent would request information from and/or about the enrollee, the agent would ascertain the enrollee's credit status based on the results of the information transaction, and the agent would communicate said results back to the merchant.

In another example, an investment company or a financial institution could be seeking to verify the identity of a customer who has forgotten his/her password to an account maintained by the institution. As part of that verification, the institution could ask for information about one of the customer's credit cards. If the customer has authorized such an information request, the institution will have that information, at least for the period required to verify identity. Then, assuming that the institution has authorized an agent, such as a credit reporting agency, to perform database dips to validate the credit card information, the institution can receive the results of this status check. In other words, the agent runs the status check on behalf of the institution.

Information Containment

A consumer may decide that certain information may be made available within a certain community of interest, but that limitations should apply to such information. In certain configurations of this invention, rules for information containment may be included in the rule-sets or explicit permissions, and these information containment rules may also be included with transferred information. These information containment rules may be enforced, for example and not by way of limitation, by contractual obligations or digital rights management (DRM). For example, a customer may wish to allow information to be used within a certain community of interest, but does not wish that information to be shared beyond that community of interest.

To continue with the example, a customer may have no problem with consumer information being shared by merchants, but in order to protect privacy, the customer would not want that information shared with insurance companies or the health care industry. In that case, any information that was the result of an information transfer request would also carry the constraint limiting the use of the information to just the initial community of interest. Other applications of constraints or permissions are envisioned. For example, NDAs (non-disclosure agreements) could identify a set of customers and requestors within which information could be shared, but outside of which information could not be shared. In this case, a package of data describing that set could also be considered information. Further, that information itself could also have privacy and notification preferences, if, for example, there are confidentiality aspects.

Location-Based-Services and Partial Information Containment

A consumer may elect to have a portion of Personal Identifying Information that would be of interest to merchants be automatically released when he enters particular merchants' environments in order to trigger certain information delivery to his mobile device for his immediate attention. Such information could, for example, be delivered to a consumer that has already downloaded an application in his mobile device that advertises his membership in a buyers club, health club, or food chain.

For instance, a person entering a fast-foot restaurant at a busy time of the day might wish to have a breakfast or lunch menu presented and automatically displayed on his mobile communications device. By making his menu selection and ordering electronically, the consumer can expect a verification message (spontaneous bill presentment) to his mobile device so he can submit an immediate authorization to pay to his bank or his non-bank financial institution functioning as his payment proxy. Right after his mobile device based payment application completes the payment by informing the merchant that money is being irrevocably transferred, he could jump the queue when his food is ready and sit down to eat.

For additional benefits, the merchant's application might require that the diner pay electronically in the most efficient manner possible. For instance, it might mean that the consumer must permit the merchant or a third party to store, aggregate, analyze and report data pertaining to his purchased menu items. In such an event, he may wish to allow a partial release of his Personal Identifying Information in order to earn valuable rewards such as coupons, rebates or game tokens that are designed to incentivize him to increase his dining frequency and or to increase the amount he spends for individual meals. Furthermore, the consumer may wish to mask his individual identity and only divulge the marketing cohort group to which he belongs.

In certain configurations of this invention, rules for information containment may be included in the rule-sets or explicit permissions, and these information containment rules prevent the transfer of certain information in the first place.

Records-keeping in the Cloud of State and Local Sales Tax Payments

Various state government legislatures have laws on the books that permit taxpayers to reduce or offset state personal income taxes when state and local sales tax payments exceed certain threshold amounts. Most consumers and small businesses today, however, do not have a convenient way to tally the percentage of every purchase that is taxed in a manner that keeps a record that is suitable for inspection and audit. When an a priori permission is granted to supply Personal Identifying Information or a subset of Personal Identifying Information in exchange for electronic transmission of detailed purchase information to a repository 'in the cloud,' there is the opportunity to register the date, value of the purchase and amount of sales tax paid as a running log entry. At tax time, this journal pertaining to the registrant's purchase behavior over a particular tax year can be queried, and every tax payment made in the registrant's state of residence can be summed and reported for tax filing purposes.

This information may be regarded as confidential and only available to the registrant himself and/or his designated tax preparation specialist. Rules set can be created to automatically trigger tax payment information gathering based on location to insure that the tally of tax payments only applies to eligible purchases.

The foregoing descriptions are meant to be illustrative and not limiting. Various changes, modifications, and additions may become apparent to the skilled artisan based upon the disclosure in this specification, and such are meant to be within the scope and spirit of the invention as defined by the appended claims.

What is claimed is:

1. A computer-implemented method comprising:
storing, in a non-transitory computer-readable storage medium, a database comprising information for an authenticated registrant comprising: (i) authenticated information identifying at least one linked credit account of the registrant, and (ii) a rule set, wherein the rule set comprises at least one explicit permission to allow customer transaction information associated with the registrant to be transferred to at least one community of interest, wherein the customer transaction information is related to a purchased item;
providing a portion of the database to a financial institution computer, the portion comprising the authenticated information identifying the at least one linked credit account, wherein the financial institution computer is configured to transmit a payment directly from a payor's account at the financial institution to the registrant's linked credit account located at a second financial institution, without using an intermediary to transfer the payment;
receiving, via at least one computer connected to a communication network, from a requestor, a request for customer transaction information associated with the registrant;
determining, via the at least one computer, based on the rule set associated with the registrant, whether requestor has permission to receive the requested customer transaction information, wherein the determination is based at least in part on which community of interest the requestor belongs to; and
transferring electronically the requested customer transaction information to the requestor, if the requestor is determined to have permission to receive the requested customer transaction information.

2. The method of claim 1 wherein said at least one explicit permission comprises the level of information that may be released and/or categories of information that may be released.

3. The method of claim 1 further comprising the step of notifying said registrant when said request from requestor is received.

4. The method of claim 3 wherein said determination of permission to receive is based at least in part on a response from said registrant to said notification.

5. The method of claim 1 wherein said information received by said requestor is used to provide a tangible benefit to said registrant.

6. The method of claim 5 wherein said tangible benefit is a coupon or rebate.

7. The method of claim 1 wherein said information received by said requestor is used for at least one of the following: authorization of a transaction, determination of payment authorization, and determination of delivery information.

8. The method of claim 1 wherein communities of interest are selected from the group of: merchants, manufacturers of goods, providers of services, and financial institutions.

9. The method of claim 1 further comprising the step of determining said at least one explicit permission for said rule set.

10. The method of claim 9 wherein said determination of said at least one explicit permission is made based on said registrant's response to one or more questions provided to said registrant.

11. The method of claim 1 wherein said registrant is an entity or person.

12. The method of claim 1 wherein said transferred information is restricted from being further transferred beyond said at least one community of interests associated with said information.

13. The method of claim 1 wherein an authorized agent may act on behalf of said registrant and/or an authorized agent may act on behalf of said requestor.

14. The method of claim 1 wherein said information related to the purchased item comprises stock-keeping unit data.

15. A system comprising:
at least one server, connected to a communication network, comprising executable programming contained on a non-transitory storage medium, said programming when executed operable to:
store a database comprising information for an authenticated registrant comprising: (i) authenticated information identifying at least one linked credit account of the registrant, and (ii) a rule set, wherein the rule set comprises at least one explicit permission to allow customer transaction information associated with the registrant to be transferred to at least one community of interest, wherein the customer transaction information is related to a purchased item;
provide a portion of the database to a financial institution computer, the portion comprising the authenticated information identifying the at least one linked credit account, wherein the financial institution computer is configured to transmit a payment directly from a payor's account at the financial institution to the registrant's linked credit account located at a second financial institution, without using an intermediary to transfer the payment;
receive, via the communication network, from a requestor, a request for customer transaction information associated with the registrant;
determine, via the server, based on the rule set associated with the registrant, whether requestor has permission to receive the requested customer transaction information, wherein the determination is based at least in part on which community of interest the requestor belongs to; and
transfer electronically the requested customer transaction information to the requestor, if the requestor is determined to have permission to receive the requested customer transaction information.

16. The system of claim 15 wherein said at least one explicit permission comprises the level of information that may be released and/or categories of information that may be released.

17. The system of claim 15 further operable to notify said registrant when said request from requestor is received.

18. The system of claim 17 wherein said determination of permission to receive is based at least in part on response from said registrant to said notification.

19. The system of claim 15 wherein said information received by said requestor is used to provide a tangible benefit to said registrant.

20. The system of claim 19 wherein said tangible benefit is a coupon or rebate.

21. The system of claim 15 wherein said information received by said requestor is used for at least one of the following: authorization of a transaction, determination of payment authorization, and determination of delivery information.

22. The system of claim 15 wherein communities of interest are selected from the group of: merchants, manufacturers of goods, providers of services, and financial institutions.

23. The system of claim 15 further operable to determine said at least one explicit permission for said rule set.

24. The system of claim 23 wherein said determination of said at least one explicit permission is made based on said registrant's response to one or more questions provided to said registrant.

25. The system of claim 15 wherein said registrant is an entity or person.

26. The system of claim 15 wherein said transferred information is restricted from being further transferred beyond said at least one community of interests associated with said information.

27. The system of claim 15 wherein an authorized agent may act on behalf of said registrant and/or an authorized agent may act on behalf of said requestor.

28. The system of claim 15 wherein said information related to the purchased item comprises stock-keeping unit data.

29. A non-transitory computer-readable storage medium comprising executable programming, wherein the executable programming instructs a computer processor to perform the following steps:
store a database comprising information for an authenticated registrant comprising: (i) authenticated information identifying at least one linked credit account of the registrant, and (ii) a rule set, wherein the rule set comprises at least one explicit permission to allow customer transaction information associated with the registrant to be transferred to at least one community of interest, wherein the customer transaction information is related to a purchased item;
provide a portion of the database to a financial institution computer, the portion comprising the authenticated information identifying the at least one linked credit account, wherein the financial institution computer is configured to transmit a payment directly from a payor's account at the financial institution to the registrant's linked credit account located at a second financial institution, without using an intermediary to transfer the payment;

receive, via the communication network, from a requestor, a request for customer transaction information associated with the registrant;

determine, via the computer processor, based on the rule set associated with the registrant, whether requestor has permission to receive the requested customer transaction information, wherein the determination is based at least in part on which community of interest the requestor belongs to; and transfer electronically the requested customer transaction information to the requestor, if the requestor is determined to have permission to receive the requested customer transaction information.

30. The non-transitory computer-readable storage medium of claim 29 wherein said information provided in response to said request for information is used to provide a tangible benefit to said registrant.

31. The non-transitory computer-readable storage medium of claim 30 wherein said tangible benefit is a coupon or rebate.

32. The non-transitory computer-readable storage medium of claim 29 wherein said received customer transaction information comprises information about a purchased item.

33. The non-transitory computer-readable storage medium of claim 29 further operable to determine at least one explicit permission to allow transaction information to be transferred to at least one community of interest, wherein said at least one explicit permission is associated with said unique identifier.

34. The non-transitory computer-readable storage medium of claim 33 wherein said at least one explicit permission comprises the level of information that may be released and/or categories of information that may be released.

35. The non-transitory computer-readable storage medium of claim 33 wherein said determination of said at least one explicit permission is made based on said registrant's response to one or more questions provided to said registrant.

36. The non-transitory computer-readable storage medium of claim 29 further operable to notify said registrant when said request from requestor is received.

37. The non-transitory computer-readable storage medium of claim 36 wherein said determination of permission is based at least in part on response from said registrant to said notification.

38. The non-transitory computer-readable storage medium of claim 29 wherein said information received by said requestor is used for at least one of the following:
authorization of a transaction, determination of payment authorization, and determination of delivery information.

39. The non-transitory computer-readable storage medium of claim 29 wherein communities of interest are selected from the group of: merchants, manufacturers of goods, providers of services, and financial institutions.

40. The non-transitory computer-readable storage medium of claim 29 wherein said transferred information is restricted from being further transferred beyond said community of interest.

41. The non-transitory computer-readable storage medium of claim 29 wherein said customer is an entity or person.

42. The non-transitory computer-readable storage medium of claim 29 wherein an authorized agent may act on behalf of said registrant and/or an authorized agent may act on behalf of said requestor.

43. The non-transitory computer-readable storage medium of claim 29 wherein said information related to the purchased item comprises stock-keeping unit data.

* * * * *